United States Patent [19]
Luce et al.

[11] Patent Number: 6,042,232
[45] Date of Patent: Mar. 28, 2000

[54] AUTOMATIC OPTOMETER EVALUATION METHOD USING DATA OVER A WIDE RANGE OF FOCUSING POSITIONS

[75] Inventors: David A. Luce, Clarence Center; Matthew Severns, Williamsville, both of N.Y.

[73] Assignee: Leica Microsystems Inc., Depew, N.Y.

[21] Appl. No.: 09/234,723

[22] Filed: Jan. 21, 1999

[51] Int. Cl.[7] ........................................................ A61B 3/10
[52] U.S. Cl. .............................................................. 351/212
[58] Field of Search ..................................... 351/200, 204, 351/205, 211, 212, 221; 356/124, 127, 124.5; 359/7, 307

[56] References Cited

U.S. PATENT DOCUMENTS

5,173,790  12/1992  Montgomery ................................. 359/7
5,331,394   7/1994  Shalon et al. ............................... 356/124

Primary Examiner—George Manuel
Attorney, Agent, or Firm—Simpson, Simpson & Snyder

[57] ABSTRACT

A method and apparatus for measuring refractive properties of a refractive optical system by fitting measurement data points to a derived function are disclosed. In a preferred embodiment relating to an automatic objective optometer, each data point represents a peak signal amplitude extracted from a scan of a plurality of pixels on an area detector array receiving light from the illuminated refractive optical system at a particular optometer position. The derived function describes a relationship between the peak pixel signal and optometer position based on changing focusing conditions of light at the detector array, which correspond to focusing conditions at an image plane of the refractive optical system under a confocal arrangement. A first derived function is applied for fast and slow sphere optometer sweeps through broad and refined ranges and includes a pair of poles at first and second astigmatic focal points to give the magnitude of sphere and cylinder powers of the eye, and a second derived function is applied for a cylinder sweep varying the axis of a non-zero cylinder component introduced to the illuminating light and includes a single pole for giving the cylinder axis.

27 Claims, 5 Drawing Sheets

Fig. 5

AUTOMATIC OPTOMETER EVALUATION METHOD USING DATA OVER A WIDE RANGE OF FOCUSING POSITIONS

BACKGROUND

A. Field of the Invention

The present invention relates generally to the field of ophthalmology, and more particularly to the field of automatic optometers and lensmeters for measuring refractive characteristics of a refractive optical system.

B. Description of the Prior Art

Automatic refractors for objectively measuring refractive properties of an eye, and automatic lensmeters for measuring refractive properties of lenses, are known to operate by introducing a beam light to the particular refractive optical system to be measured and detecting its influence on the beam due to refraction. In the case of objective refractors, also referred to as objective optometers, it is known to provide a light source and a plurality of optical elements defining an illuminating optical path to the eye, and a matching plurality of optical elements defining a detecting optical path from the eye to a detector, whereby all or part of an image of the light source formed on the retina is detected through retro-reflection on the detector. The vergence of the illuminating beam is varied by moving certain of the optical elements of the optometer through a range of positions to cause focusing of the light source by the eye at different locations relative to the retina, so that an optometer position where a "best focus" occurs at the retina can be found. As will be understood by those familiar with the art, the optical elements define a Badal system. The vergence of the illuminating beam is expressed in terms of diopters. In this way, the amount of spherical refractive error is determined. A similar "best focus" procedure is followed for determining the amount of cylinder refractive error and its angular orientation or axis by rotating pairs of oppositely powered cylinder lenses about the illuminating and detecting optical paths.

Heretofore, automatic objective optometers have generally relied on principles of repetitive measurement, whereby the optometer position at which a maximum detector signal is received is recorded over and over again for repeated measurement cycles of the instrument with respect to the same eye, and a statistical evaluation of the results is performed to reach a single overall value for the best focus optometer position. This approach involves substantial complexity, and it ignores signal information available throughout the full range of optometer positions and the expected behavior of same. Moreover, modulative noise due to individual sensitivity of detector elements (pixels) remains a factor which affects measured values.

SUMMARY OF THE INVENTION

Accordingly, it is a primary object of the present invention to provide an improved evaluation method and apparatus employing this method for use in determining the refractive properties of a refractive optical system, such as that of an eye.

Briefly, the present invention involves a method and apparatus for estimating refractive properties of a refractive optical system by fitting measurement data points to a derived function. In a preferred embodiment relating to an automatic objective optometer, each data point represents a peak signal amplitude extracted from a scan of a plurality of pixels on an area detector array receiving light from the illuminated refractive optical system at a particular optometer position. The derived function describes a relationship between the peak pixel signal and optometer position based on changing focusing conditions of light at the detector array, which correspond to focusing conditions at an image plane of the refractive optical system under a confocal arrangement. In the objective optometer of the preferred embodiment, a first derived function is applied for fast and slow sphere optometer sweeps through broad and refined ranges and includes a pair of poles at first and second astigmatic focal points to give the magnitude of sphere and cylinder powers of the eye, and a second derived function is applied for a cylinder sweep varying the axis of a non-zero cylinder component introduced to the illuminating light and includes a single pole for giving the cylinder axis.

BRIEF DESCRIPTION OF THE DRAWINGS

The nature and mode of operation of the present invention will now be more fully described in the following detailed description of the preferred embodiments taken with the accompanying drawing figures, in which.

DETAILED DESCRIPTION OF THE PREFERRED EMBODIMENTS

Figure 1:
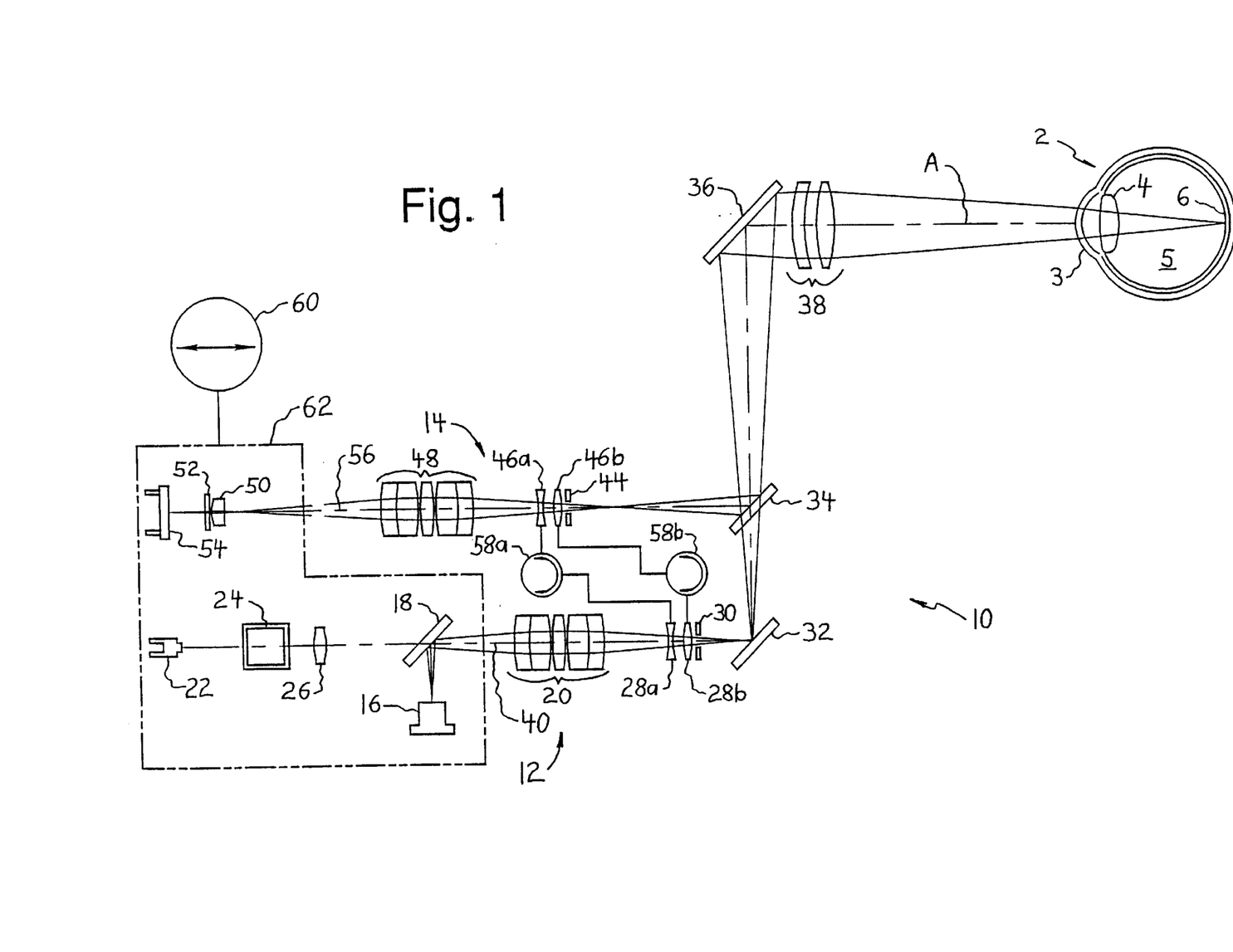
FIG. 1 is an optical schematic diagram of an objective optometer formed in accordance with a preferred embodiment of the present invention.

Reference is made initially to FIG. 1 of the drawings, wherein an apparatus formed in accordance with a preferred embodiment of the present invention is shown and designated generally by the reference numeral 10. Apparatus 10 of the preferred embodiment is an objective optometer for measuring refractive errors of the refractive optical system of an eye 2, shown as including a cornea 3, crystalline lens 4, vitreous humor 5, and retina 6. Optometer 10 is of a type which monitors source light retro-reflected from the fundus of the eye over a range of different sphere and cylinder focusing conditions to determine the particular sphere and cylinder focusing conditions at which a "best focused image" is produced on the retina. While the preferred embodiment of the present invention is described in the context of an objective optometer for measuring refractive errors in an eye through retro-reflection, it will be readily appreciated from this description that the present invention may also be applied to lensmeters for measuring refractive characteristics of lenses, particularly ophthalmic corrective lenses, without use of retro-reflection.

Optometer 10 of the preferred embodiment, represented schematically in FIG. 1, generally comprises an illuminating optical system 12 for illuminating eye 2, and a detecting optical system 14 for detecting light retro-reflected from the eye.

Illuminating optical system 12 includes a point light source 16, preferably a super luminescent diode (SLD) emitting light in the near infra-red spectral region, arranged to face a beamsplitter 18 angled to reflect light from source 16 toward a primary optometer lens 20 consisting of a pair of biconvex positive doublets on opposite sides of a biconvex positive singlet. A target illuminating source 22 is preferably arranged to illuminate a target reticle 24 in front of an aspheric lens 26 positioned along a light transmitting direction of beamsplitter 18, whereby a fixation target may be presented to the test subject coincident with illuminating light rays from source 16. Light exits optometer lens 20 and travels through a pair of cooperating cylinder lenses 28a, 28b of opposite cylinder power and a restricting aperture 30 before being redirected by a reflecting mirror 32. The redirected light is transmitted through a beamsplitter 34 and then reflected by another beamsplitter 36 along a test axis A of the optometer in the direction of eye 2. The illuminating light travels along test axis A through a relay lens system 38, which serves to focus restricting aperture 30 at the surface of cornea 3 and translate the always positive vergence (converging) light reflected by beam splitter 36 to either positive or negative vergence (diverging) light, depending upon the sphere optometer position discussed below. The illuminating light passes through lens system 38 to reach eye 2. Accordingly, an illuminating optical path 40 is defined from source 16 to retina 6. A portion of illuminating optical path 40 shown for the preferred embodiment is designed to be spaced from test axis A of the optometer along which eye 2 is aligned for reasons unrelated to the present invention.

Detecting optical system 14 coincides physically with illuminating optical system 12 in reverse direction from retina 6 back to beamsplitter 34. At beamsplitter 34, the retro-reflected light is redirected through a restricting aperture 44, a pair of cooperating cylinder lenses 46a,46a of opposite cylinder power, an optometer lens 48 nominally identical to optometer lens 20, a relay lens 50, and an infra-red pass filter 52 to reach a light-sensitive detector 54. Accordingly, a detecting optical path 56 is defined from retina 6 to detector 54. Light-sensitive detector 54 is preferably a two-dimensional area detector having a plurality of light-sensitive pixels each of which generates an output voltage signal representative of the intensity of light energy received by the pixel. Detector 54 is positioned at a complementary optical position relative to light source 16, whereby light retro-reflected from eye 2 passes through the same optical configuration, in reverse, as source light illuminating the eye. Therefore, when an image of light source 16 is well-focused on retina 6, the retro-reflected light will be well-focused on detector 54 in this confocal arrangement.

Optometer 10 further includes a negative cylinder motor 58a, a positive cylinder motor 58b, and a sphere motor 60. Negative cylinder motor 58a is a stepper motor operably coupled to negative cylinder lenses 28a and 46a for driving rotation of the negative cylinder lenses about illuminating optical path 40 and detecting optical path 56, respectively, in synchronized stepwise fashion. Likewise, positive cylinder motor 58b is a stepper motor operably coupled to positive cylinder lenses 28b and 46a for driving rotation of the positive cylinder lenses about illuminating optical path 40 and detecting optical path 56, respectively, in synchronized stepwise fashion. Therefore, negative cylinder lens 28a may be rotated relative to positive cylinder lens 28b such that their respective cylinder axes are non-parallel to produce non-zero cylinder vergence or power, and both cylinder lenses 28a and 28b may be rotated together as a pair to vary the overall cylinder axis of the resultant non-zero cylinder power. In this way, a cylinder component may be introduced to the illuminating light incident upon eye 2, and the angular orientation (axis) of the cylinder component may be varied through a range of 180 degrees. To maintain a confocal optical system, cylinder lenses 46a,46a are rotated by cylinder motors 58a,58b about detecting optical path 56 in synchrony with the rotation of cylinder lenses 28a,28b about illuminating optical path 40.

Sphere motor 60 is operably coupled to a carrier 62 which supports light source 16, beamsplitter 18, target illuminating source 22, target reticle 24, aspheric lens 26, relay lens 50, filter 52, and detector 54. Sphere motor 60 drives carrier 62 linearly back and forth though a range of linear positions along a path parallel to respective portions of illuminating optical path 40 and detecting optical path 56 on which optometer lenses 20 and 48 are aligned. Since light source 16 and beamsplitter 18 travel the same distance relative to optometer lens 20 that relay lens 50, filter 52, and detector 54 travel relative to optometer lens 48, the complementary optical relationship between light source 16 and detector 54 is maintained regardless of the position of carrier 62 through its range of linear travel. As will be understood by those skilled in the art, movement of carrier 62 is equivalent to moving light source 16 in "Badal" optical space. In the preferred embodiment, the linear optometer position is expressed in terms of diopters.

By way of overview, spherical refractive error of the eye is determined by finding the linear position of light source 16 and detector 54, relative to a normal reference position, which produces a best focused image (focal point) at retina 6 and at detector 54 under the confocal system described above. The linear optometer position producing a best focused image at retina 6 corresponds in magnitude to spherical refractive error of the eye and is expressed in diopters. The normal reference position is at zero diopters and a maximum test range of from −20 to +20 diopters is provided in the preferred embodiment. In an astigmatic eye, a second focal point is distinguishable from the first focal point as the optometer is adjusted through its range of linear motion and the difference in linear optometer positions corresponds in magnitude to the cylinder refractive error of the eye. In an eye without astigmatism, that is to say without cylinder power, the two focal points mentioned above collapse into a single focal point corresponding in magnitude to the spherical refractive error. Cylinder axis of the eye is determined by introducing light at a given vergence representing a non-zero cylinder power by adjusting negative and positive cylinder lenses 28a,28b to a corresponding rotational position relative to one another, and then rotating both cylinder lenses 28a,28b together through 180 degrees to vary the cylinder axis of the incident light to find the angular position at which best focus occurs. In keeping with the present invention, numerical curve fits are performed to evaluate peak pixel data points generated during a linear optometer sweep to calculate sphere and cylinder powers, and to evaluate peak pixel data generated during the rotational sweep to calculate cylinder axis and provide a second, independent determination of cylinder power. Since it is possible to vary the vergence of illuminating light other than by using sweeps as described above which are linear and rotational in nature, the term "sphere sweep" is used hereinafter to refer to a sweep, whether linear or not, conducted to vary spherical vergence of the illuminating beam, and the term "cylinder sweep" is used hereinafter to refer to a sweep which varies the axis of a non-zero cylinder component.

Figure 2:
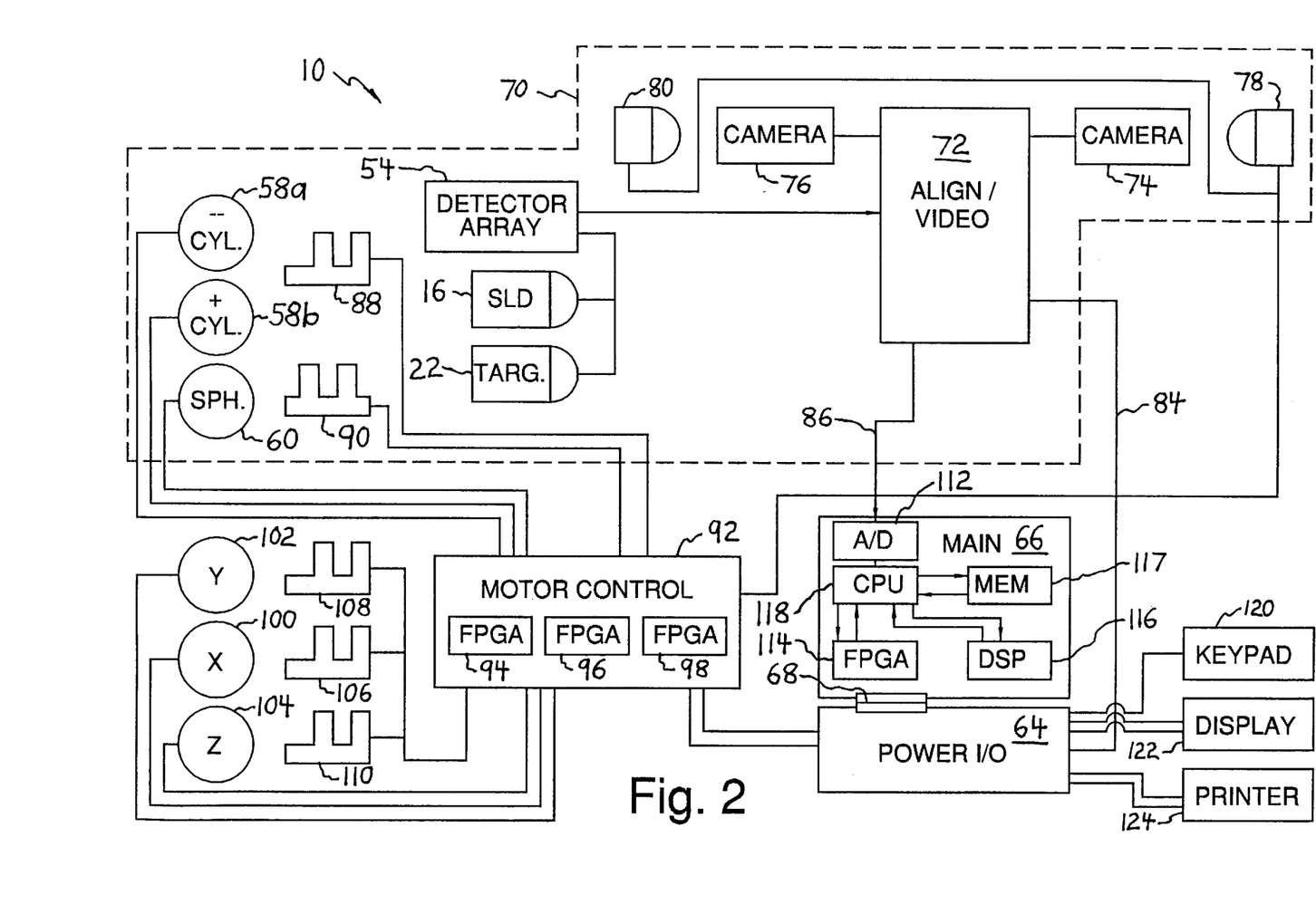
FIG. 2 is an electronic block diagram of the objective optometer shown in FIG. 1.

FIG. 2 is an electrical block diagram of objective optometer 10. A power input/output circuit 64 and main control circuit 66 are connected by data bus 68. An optical head assembly 70, shown generally in broken line, comprises an alignment/video control circuit 72 for processing video information from a pair of alignment cameras 74 and 76 connected thereto. The alignment cameras 74 and 76 cooperate with a pair of alignment illumination sources 78 and 80 for purposes of instrument alignment with the eye, as taught in commonly owned U.S. Pat. No. 4,881,807. Optical head assembly 70 further comprises light source 16, detector 54, and target illuminating source 22 all connected to alignment/video control circuit 72. Power is fed from input/output circuit 64 to alignment/video control circuit 72 along line 84, while transfer of control and measurement data between alignment/video control circuit 72 and main control circuit 66 takes place along line 86. Optical head assembly 70 also includes negative cylinder motor 58a, positive cylinder motor 58b, and sphere motor 60, as well as a cylinder limit switch 88 for setting a reference for one of the cylinder lens pairs 28a,28b and 46a,46b, and a sphere limit switch 90 for limiting linear travel of carrier 62. Negative cylinder motor 58a, positive cylinder motor 58b, sphere motor 60, cylinder limit switch 88, and sphere limit switch 90 are each connected to a motor control circuit 92. Three field programmable gate arrays (FPGAs) 94, 96, and 98 are provided as part of motor control circuit 92 for generating synthesized quadrature sine waves to drive stepper motors 58a, 58b, and 60, and for tracking the precise step location of each motor, respectively. As may be seen in FIG. 2, an X-axis motor 100, a Y-axis motor 102, and a Z-axis motor 104 are also driven by motor control circuit 92 within ranges dictated by associated X, Y, and Z limit switches 106, 108, and 110 in order to align test axis A with eye 2.

Extraction and processing of measurement data in accordance with the present invention is carried out by an A/D converter 112, a FPGA 114, a digital signal processor (DSP) 116, and a programmable memory (EPROM) 117 under the control of a central processing unit (CPU) 118 in main control circuit 66. FPGA 114 receives digitized pixel signals from AID converter 112 and extracts a peak pixel signal for each scan of detector array 54 in real time by comparing the amplitude of each serially received pixel signal with a previously held peak pixel amplitude for that scan, and registering a new peak pixel amplitude if the comparison warrants. The resulting peak pixel amplitude for each scan is held in registry with a corresponding optometer position to provide a single data point. A plurality of data points are extracted during each optometer sweep, and DSP 116 performs a simplex curve fit of the extracted data points to a derived function according to a routine stored in programmable memory 117. As described below, curve fit of data from a sphere optometer sweep allows calculation of sphere and cylinder powers, and curve fit of data from a cylinder optometer sweep allows calculation of cylinder axis as well as a second, independent determination of cylinder power.

Also shown schematically in the diagram of FIG. 2 are a keypad input 120 for operator control of optometer 10, a display device 122, such as an integral LCD display arranged to face the operator, and a printer 124 for providing hard copy output of measurement results.

Operation of optometer 10 and calculation of the refractive characteristics will now be described. Once test axis A is positioned in alignment with eye 2, an optometer measurement cycle is initiated either automatically by the alignment system or manually by the operator. During an optometer measurement cycle, motors 58a, 58b, and 60 are driven in a predetermined operation sequence as described below to enable calculation of sphere and cylinder powers and cylinder axis.

The first portion of the optometer measurement cycle is a rapid sphere sweep wherein negative and positive cylinder lenses 26a,26b are set to cancel each other out for zero overall cylinder, and sphere motor 60 drives moving carrier 62 through a series of equally spaced linear positions over a predetermined, relatively broad range, for example from −10 through +10 diopters. Detector array 54 is scanned at a fixed frame rate, for example 50 Hz, and a peak pixel amplitude, converted by A/D converter 112 to a digitized value ranging from 0–255, is extracted by FPGA 114. This peak pixel information, together with corresponding optometer sphere position information, is provided to DSP 116 asynchronously to be processed according to a multidimensional numerical curve fit described herein. In a preferred rapid measurement cycle, sphere motor 60 moves the equivalent of 0.0635 diopters every step. In a fast sweep, the sphere motor 60 moves approximately 12 steps per scan, and a motor interrupt signal is sent at the completion of each detector scan, such that a data point is generated at approximately every 0.76 diopters along the range.

During a sphere optometer sweep, the area on detector 54 illuminated by the retro-reflected beam changes as the varying vergence light is focused by the eye at different locations relative to retina 6. Intuitively, as the area on detector 54 illuminated by the retro-reflected beam becomes larger due to poorer focusing, the total light energy received by the detector is spread out among a greater number of pixels, and thus the peak pixel amplitude will decrease. Conversely, as the illuminated area on detector 54 becomes smaller due to better focusing, the total light energy received by the detector is confined to fewer pixels, and thus the peak pixel amplitude will increase. Since the peak pixel amplitude at a particular optometer position is proportional to the reciprocal of the total illuminated area on detector 54, it can be shown that the peak pixel amplitude as a function of sphere optometer position (z) is expressed to a very good approximation by the following relation:

$$PP(z) = \frac{M}{\left(1 - \frac{z}{f_1} + A\right)\left(1 - \frac{z}{f_2} + A\right)} + O \quad z < f_1; z < f_2$$

$$PP(z) = \frac{M}{\left(-1 + \frac{z}{f_1} + A\right)\left(1 - \frac{z}{f_2} + A\right)} + O \quad z > f_1; z < f_2$$

$$PP(z) = \frac{M}{\left(-1 + \frac{z}{f_1} + A\right)\left(-1 + \frac{z}{f_2} + A\right)} + O \quad z > f_1; z > f_2$$

where PP is the digitized peak pixel amplitude ranging from 0–255, z is the optometer position in diopters, $f_1$ is the location of a first astigmatic focal point in diopters, $f_2$ is the location of a second astigmatic focal point in diopters, M is a magnitude scaling factor assumed constant for any given scan, A is a dimensionless effective source size parameter less than one, and O is a relatively small system offset value assumed constant for any given scan. In the above equation, $f_1$ and $f_2$ give the magnitudes of the sphere and cylinder refractive errors. More specifically, in "positive cylinder mode", the eye is said to have $f_1$ diopters of spherical power and $f_2-f_1$ diopters of cylinder power; in "negative cylinder mode", the eye is said to have $f_2$ diopters of spherical power and $f_1-f_2$ diopters of cylinder power. An initial value for offset O can be zero. Starting values for M and A can be determined by assigning rough values for $f_1$ and $f_2$ based on the clustering of higher amplitude data points and solving for M and A. As will be appreciated from description to follow, the above function results in a pair of poles at $f_1$ and $f_2$.

The peak pixel signal data points are fitted to the derived function listed above by DSP 116 using a simplex numerical curve fitting software routine stored in programmable memory 117 to arrive at values for the focal points $f_1$ and $f_2$. A preferred curve fitting algorithm is a downhill simplex method published by J. A. Nelder and R. Mead in *Computer Journal*, vol. 7, pages 308–313 (1965). A description of this algorithm and example software code in the "C" language may be found in *Numerical Recipes in C: The Art of Scientific Computing*, $2^{nd}$ edition, copyright 1992 Cambridge University Press, pages 408–412.

As a result of this initial fast sphere sweep, crude values of sphere and cylinder powers are determined by finding values of the focal points $f_1$ and $f_2$. The crude values of sphere and cylinder powers are then used to select a more narrow range within the region of interest, for example by starting at −3 diopters from the first focal point $f_1$ and moving through +3 diopters from the second focal point $f_2$. In a second portion of the optometer measurement cycle, sphere motor 60 is commanded to drive carrier 62 through a slow, refined sphere sweep over the narrowed range. In the slow sweep of the preferred embodiment, the sphere motor 60 moves approximately 3 steps per scan, and a motor interrupt signal is sent at the completion of each detector scan, such that a data point is generated at approximately every 0.19 diopters along the range. Peak pixel data points from the refined sweep are subjected to the same simplex curve fitting procedure as described above for the initial fast sweep to provide a final determination of sphere and cylinder powers of the refractive optical system of the eye.

Once the fast and slow sphere sweeps have been performed, the sphere optometer position is adjusted to a spherical equivalent position of the eye mid-way between focal points $f_1$ and $f_2$, and a non-zero cylinder component is introduced to the illuminating light, for example two diopters of cylinder, by effecting relative rotation between negative and positive cylinder lenses 28a and 28b. A third portion of the optometer measurement cycle comprises a cylinder sweep of the cylinder lens pair 28a,28b about illuminating optical axis 40 to vary the effective angle of the non-zero cylinder component from zero degrees to 180 degrees. In a currently preferred measurement cycle, cylinder motors 58a,58b rotate cylinder lenses 28a,28b (as well as corresponding cylinder lenses 46a,46b) in discreet steps equivalent to 0.76 degrees. Intuitively, as the angular orientation of the instrument cylinder component approaches the same angular orientation as cylinder axis of the eye, the area on detector 54 illuminated by the retro-reflected beam becomes smaller due to improved focusing. Consequently, the total light energy received by the detector is confined to fewer pixels, and thus the peak pixel amplitude approaches a maximum value. Since the peak pixel amplitude at a particular angle of the optometer cylinder component is proportional to the reciprocal of the total illuminated area on detector 54, it can be shown that the peak pixel amplitude as a function of optometer cylinder angle (Θ) is expressed to a very good approximation by the following relation:

$$PP(\Theta) = \frac{M}{(1 - CR * \sin(\Theta - T))^2}$$

where PP is the digitized peak pixel amplitude ranging from 0–255, Θ is the optometer cylinder angle, T is the angle of the eye cylinder, CR is a "cylinder ratio" defined as the eye cylinder power/instrument cylinder power, and M is an arbitrary scaling constant. In the cylinder sweep, the cylinder motors 58a,58b move approximately 7 steps per detector scan, such that a data point is generated at approximately every 5 degrees of rotation through the angular range.

Similar to the sphere sweeps, the peak pixel signal data from the cylinder sweep is fitted to the derived angular intensity function by DSP 116 using an analogous simplex numerical curve fitting software routine stored in programmable memory 117 to arrive at a value for eye cylinder axis T as well as cylinder ratio CR. Since the denominator of the cylinder ratio CR is a known value corresponding to the non-zero instrument cylinder component, it will be appreciated by the reader that the determination of cylinder ratio CR by the multidimensional curve fit permits separate calculation of the magnitude of eye cylinder power independently of the calculation of this property via the sphere sweeps and data curve fits associated therewith.

The sphere and cylinder powers and the cylinder axis are then reported as properties of the eye, or as prescription powers for corrective lenses for the eye, by reporting means such as display device 122 and a printer 124.

Figure 3:
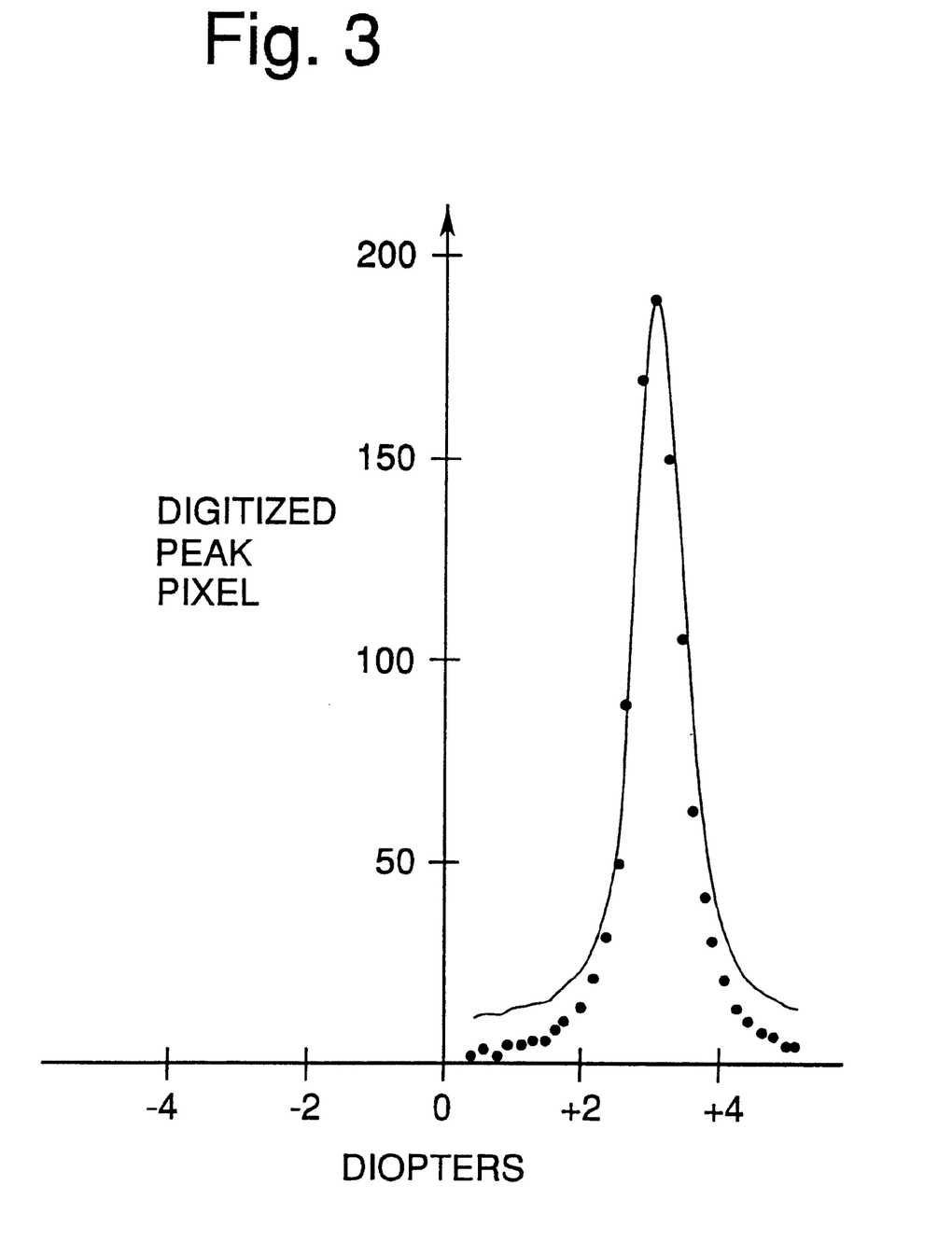
FIG. 3 is a graph illustrating a sphere sweep curve fit of measurement data for an emmetropic eye.
Figure 4:
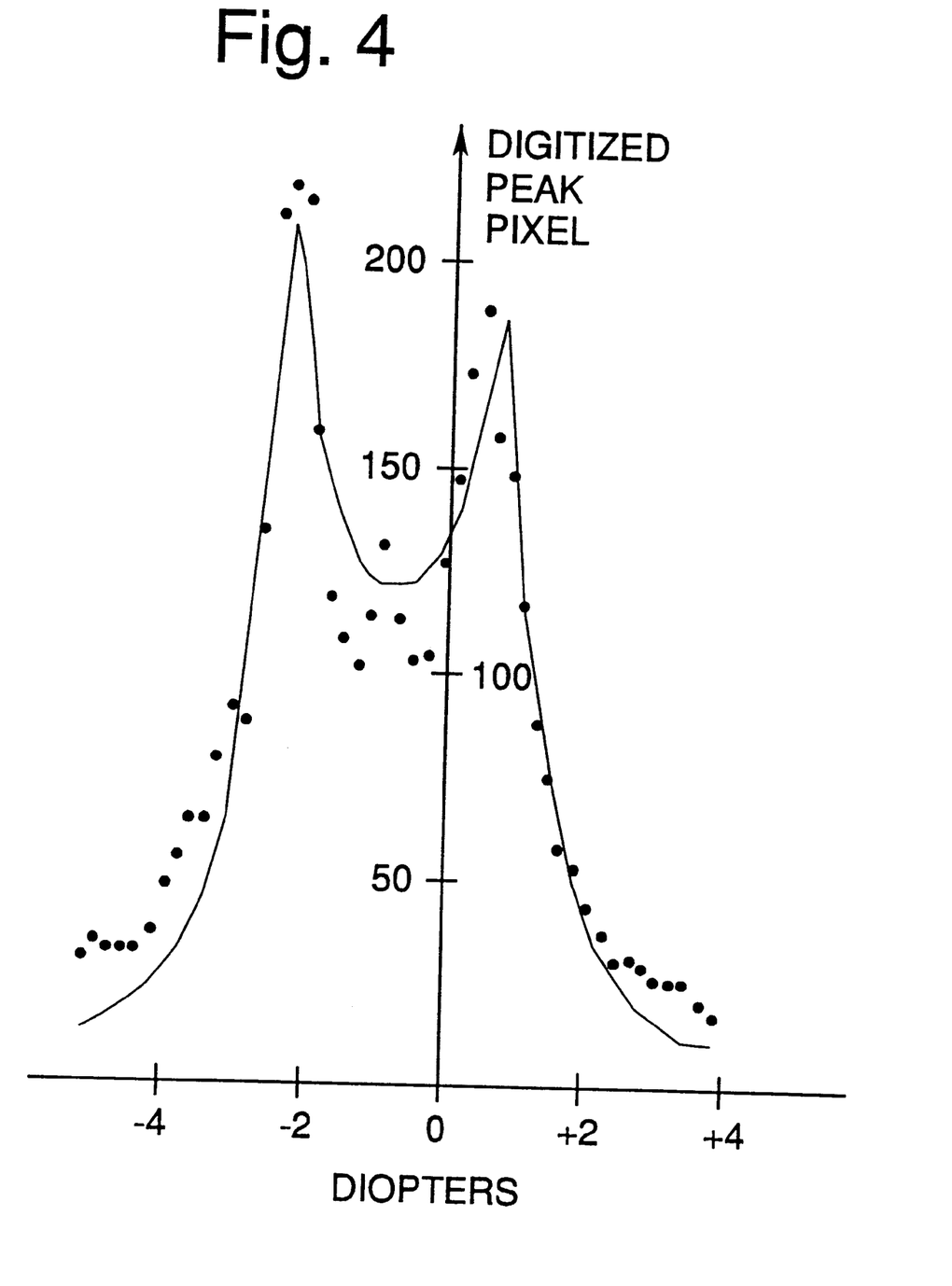
FIG. 4 is a graph illustrating a sphere sweep curve fit of measurement data for an eye having astigmatism.
Figure 5:
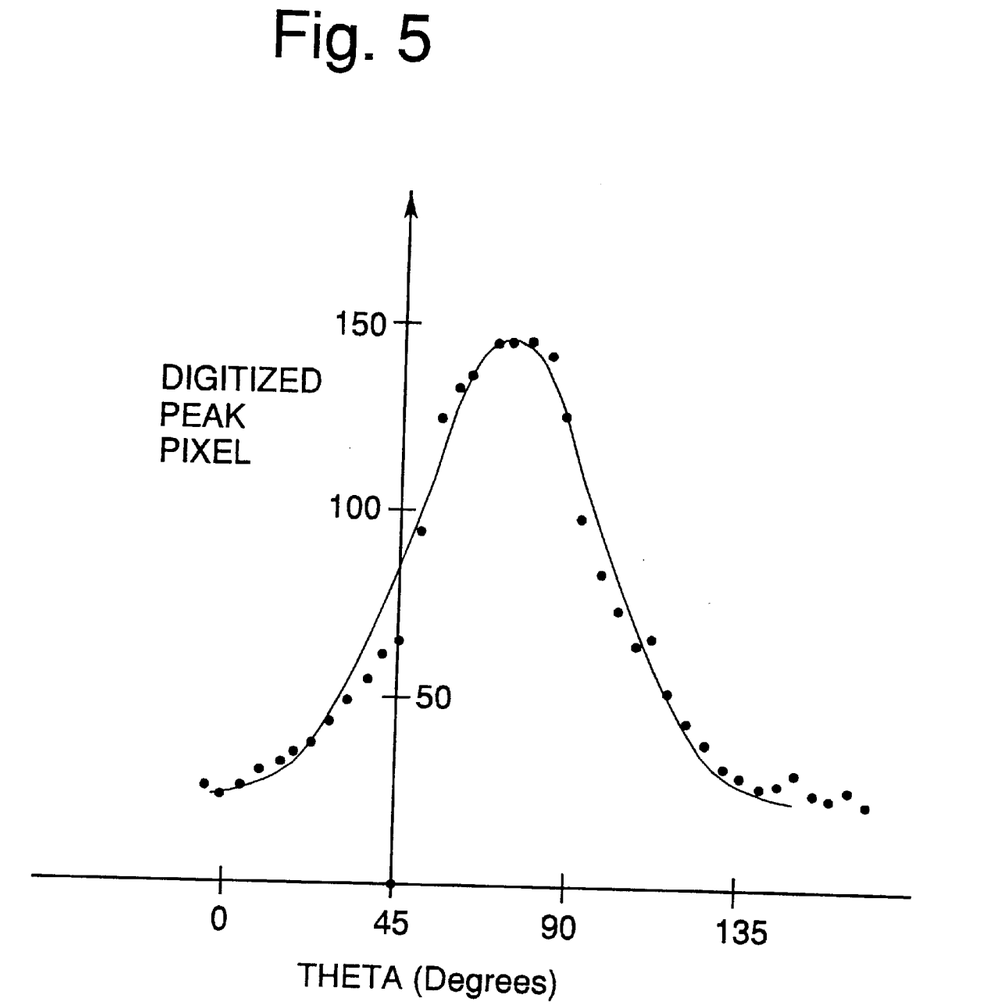
FIG. 5 is a graph illustrating a cylinder sweep curve fit of measurement data for an eye having astigmatism.

Examples of measurement and curve fit results are presented in the graphs shown in FIGS. 3–5. FIG. 3 is a plot of peak pixel signal as a function of optometer position for a sphere sweep measuring an emmetropic eye, that is to say an eye having normal no cylinder power. The resultant curve generated by the curve fitting routine is also shown. Since the eye is virtually without astigmatism, only a single pole is readily apparent in the curve corresponding to the single focal point. Stated differently, both focal points $f_1$ and $f_2$ are at almost the same location. The pole occurs at just over +3 diopters of sphere power. The plot of FIG. 4 was taken from a measurement of an eye having astigmatism. As may be seen, the curve to which the data points are fitted includes a pair of separated poles corresponding to focal points $f_1$ and $f_2$. The measured eye has a sphere power of −2.134 diopters and a cylinder power of +2.822 diopters in positive cylinder mode. Finally, FIG. 5 presents plotted data points and a resultant fitted curve for a cylinder measurement sweep of an astigmatic eye. The analysis indicates a cylinder axis at about 72 degrees.

The present invention makes use of the large number of data points gathered in a single sphere or cylinder sweep to generate a more precise measurement in a shorter time than was possible under the prior art. The locations of the focal points and cylinder axis are determined to precision greater than the spacing of the original data points because the generic forms of the functional relationships governing the data is known. Moreover, the curve fitting process of the present invention automatically determines and compensates for arbitrary system offsets and scaling factors. The determination of radiometric information reflected from the eye is intrinsically unstable near the focal points, because the area of scattering reflection from the retina becomes very small and very sensitive to localized retinal morphology; the curve fitting routine averages through this effect in an optimum manner because of the knowledge of the generic data relationships.

What is claimed is:

1. A method of determining refractive properties of a refractive optical system comprising the steps of:

A) illuminating said refractive optical system with light rays from a source and progressively varying the vergence of said light rays through a range to change the intensity distribution of light at an image plane of said refractive optical system;

B) detecting an image of said source formed by said refractive optical system to provide signal information indicative of said changing intensity distribution of light at said image plane;

C) extracting detected intensity signal information corresponding to varying degrees of vergence of said light rays to provide a plurality of data points;

D) estimating said refractive properties of said refractive optical system by fitting said data points to a derived function; and E) reporting said refractive properties.

2. A method of determining refractive properties according to claim 1, wherein said image of said source is detected by a two-dimensional area detector having an array of light-sensitive pixels, and said intensity signal information comprises a peak pixel signal extracted for each corresponding degree of vergence.

3. A method of determining refractive properties according to claim 1, wherein step (B) includes detecting a retro-reflected image of said source.

4. A method of determining refractive properties according to claim 3, wherein said refractive optical system is that of a human eye, and said image plane is defined by a retina of said eye.

5. A method of determining refractive properties according to claim 4, wherein said image of said source is detected by a two-dimensional area detector having an array of light-sensitive pixels, and said intensity signal information comprises a peak pixel signal extracted for each corresponding degree of vergence.

6. A method of determining refractive properties according to claim 1, wherein sphere and cylinder powers of said refractive optical system are determined.

7. A method of determining refractive properties of a refractive optical system comprising the steps of:

A) illuminating said refractive optical system with light rays from a source, said light rays having a non-zero cylinder component;

B) progressively varying an angular orientation of said cylinder component through a range to change the intensity distribution of light at an image plane of said refractive optical system;

C) detecting an image of said source formed by said refractive optical system to provide signal information indicative of said changing intensity distribution of light at said image plane;

D) extracting detected intensity signal information corresponding to varying angles of orientation of said cylinder component to provide a plurality of data points;

E) estimating said refractive properties of said refractive optical system by fitting said data points to a derived function; and F) reporting said refractive properties.

8. A method of determining refractive properties according to claim 7, wherein said image of said source is detected by a two-dimensional area detector having an array of light-sensitive pixels, and said intensity signal information comprises a peak pixel signal extracted for each corresponding angle of orientation of said cylinder component.

9. A method of determining refractive properties according to claim 7, wherein step (C) includes detecting a retro-reflected image of said source.

10. A method of determining refractive properties according to claim 9, wherein said refractive optical system is that of a human eye, and said image plane is defined by a retina of said eye.

11. A method of determining refractive properties according to claim 10, wherein said image of said source is detected by a two-dimensional area detector having an array of light-sensitive pixels, and said intensity signal information comprises a peak pixel signal extracted for each corresponding angle of orientation of said cylinder component.

12. A method of determining refractive properties according to claim 7, wherein cylinder power and cylinder axis of said refractive optical system are determined.

13. An apparatus for determining refractive properties of a refractive optical system comprising:

a light source;

a light-sensitive detector for generating a signal representative of the intensity of light received thereby;

an illuminating optical path from said light source to said refractive optical system for delivering rays of light from said light source to said refractive optical system;

a detecting optical path from said refractive optical system to said detector for delivering rays of light from said refractive optical system to said detector;

means for changing an optical position of said light source relative to said refractive optical system to vary the vergence of said rays of light incident upon said refractive optical system;

processing means for extracting said signal generated by said detector for each of a plurality of corresponding optical positions of said light source to provide a plurality of data points, and for fitting said data points to a derived function to estimate said refractive properties; and means for reporting said refractive properties.

14. An apparatus for determining refractive properties according to claim 13, wherein said detector is a two-dimensional area detector having an array of light-sensitive pixels, and said processing means includes peak detector means for extracting a peak pixel signal for each corresponding optical position of said light source.

15. An apparatus for determining refractive properties according to claim 13, wherein said means for changing an optical position of said light source includes a stepper motor drivably connected to said light source for moving said light source in discreet steps.

16. An apparatus for determining refractive properties according to claim 13, wherein said detecting optical path is followed by light retro-reflected from said refractive optical system.

17. An apparatus for determining refractive properties according to claim 16, wherein said refractive optical system is that of a human eye, and said image plane is defined by a retina of said eye.

18. An apparatus for determining refractive properties according to claim 17, wherein said detector is a two-dimensional area detector having an array of light-sensitive pixels, and said processing means includes peak detector means for extracting a peak pixel signal for each corresponding optical position of said light source.

19. An apparatus for determining refractive properties according to claim 13, wherein said reporting means reports sphere and cylinder powers of said refractive optical system.

20. An apparatus for determining refractive properties of a refractive optical system comprising:

a light source;

a light-sensitive detector for generating a signal representative of the intensity of light received thereby;

an illuminating optical path from said light source to said refractive optical system for delivering rays of light from said light source to said refractive optical system;

a detecting optical path from said refractive optical system to said detector for delivering rays of light from said refractive optical system to said detector;

means for introducing a non-zero cylinder component to said rays of light incident upon said refractive optical system;

means for varying an angular orientation of said cylinder component through a range to change the intensity distribution of light at an image plane of said refractive optical system;

processing means for extracting said signal generated by said detector for a plurality of corresponding angular orientations of said cylinder component to provide a plurality of data points, and for fitting said data points to a derived function to estimate said refractive properties; and means for reporting said refractive properties.

21. An apparatus for determining refractive properties according to claim 20, wherein said detector is a two-dimensional area detector having an array of light-sensitive pixels, and said processing means includes peak detector means for extracting a peak pixel signal for each corresponding angular orientation of said cylinder component.

22. An apparatus for determining refractive properties according to claim 20, wherein said means for introducing a cylinder component includes a pair of opposing cylinder lenses located on said illuminating optical path.

23. An apparatus for determining refractive properties according to claim 22, wherein said means for varying an angular orientation of said cylinder component includes a pair of stepper motors connected one to each of said pair of cylinder lenses for rotating said cylinder lenses about said illuminating optical path in discreet angular steps.

24. An apparatus for determining refractive properties according to claim 20, wherein said detecting optical path is followed by light retro-reflected from said refractive optical system.

25. An apparatus for determining refractive properties according to claim 24, wherein said refractive optical system is that of a human eye, and said image plane is defined by a retina of said eye.

26. An apparatus for determining refractive properties according to claim 25, wherein said detector is a two-dimensional area detector having an array of light-sensitive pixels, and said processing means includes peak detector means for extracting a peak pixel signal for each corresponding angular orientation of said cylinder component.

27. An apparatus for determining refractive properties according to claim 20, wherein said reporting means reports cylinder power and cylinder axis of said refractive optical system.

* * * * *